United States Patent [19]
Zuckerman et al.

[11] 3,948,248
[45] Apr. 6, 1976

[54] METHOD OF MEASURING OCULAR PULSE

[76] Inventors: Joel L. Zuckerman, 788 Farmington Ave., West Hartford, Conn. 06119; Harry J. Grossman, 49 Walden R.F.D. 1, West Willington, Conn. 06279

[22] Filed: Sept. 5, 1974

[21] Appl. No.: 503,363

[52] U.S. Cl. .................... 128/2 T; 73/67.7; 128/2 V
[51] Int. Cl.² .......................................... A61B 10/00
[58] Field of Search ..... 128/2 T, 2 V, 2.05 Z, 24 A; 73/80, 67.8 R, 67.6, 67.7

[56] References Cited
UNITED STATES PATENTS

| | | |
|---|---|---|
| 3,237,623 | 3/1966 | Gordon ......................... 73/67.8 R X |
| 3,371,660 | 3/1968 | Carlin ................................. 128/2 T |
| 3,379,901 | 4/1968 | Richards ..................... 128/2.05 Z X |
| 3,453,998 | 7/1969 | Giglio .................................. 128/2 T |
| 3,596,504 | 8/1971 | Frey .................................. 73/67.8 R |
| 3,631,849 | 1/1972 | Norris ............................ 128/2.05 R |
| 3,690,158 | 9/1972 | Lichtenstein et al. .......... 128/2 V X |
| 3,763,851 | 10/1973 | Haff et al. ..................... 128/2.05 Z |

*Primary Examiner*—Kyle L. Howell

[57] ABSTRACT

A method of obtaining a reading of the ocular pulse in its unbiased, natural state by transmitting continuous wave ultrasonic energy to the eye from a source spaced from the eye, receiving said energy reflected back from said eye, and detecting a modulation in said relected energy caused by pulsations of said eye.

6 Claims, 9 Drawing Figures

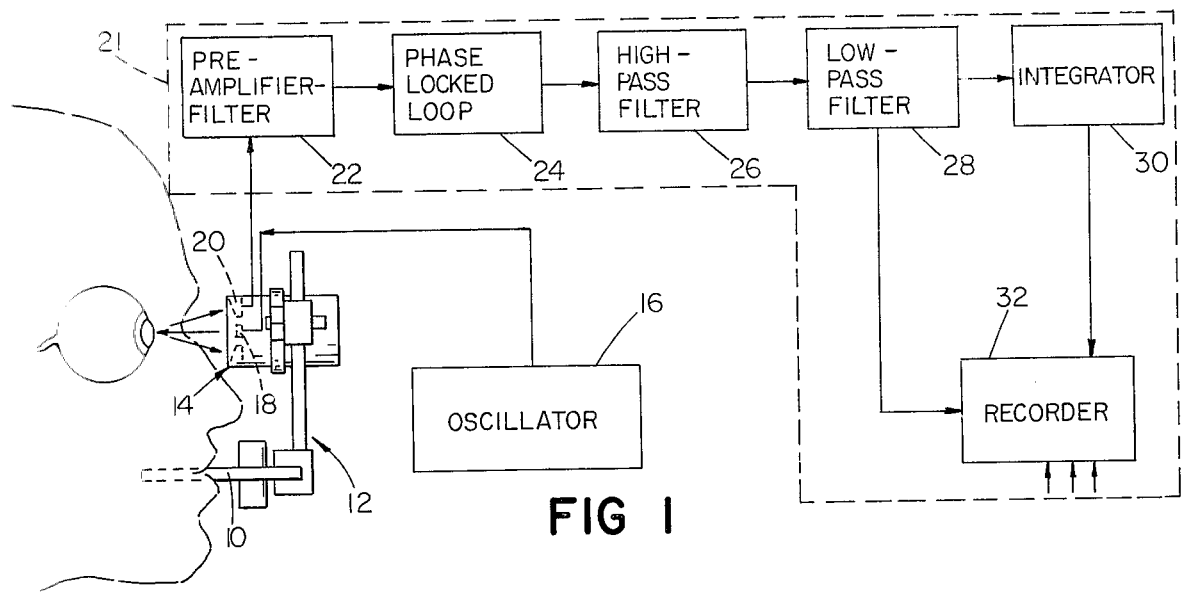
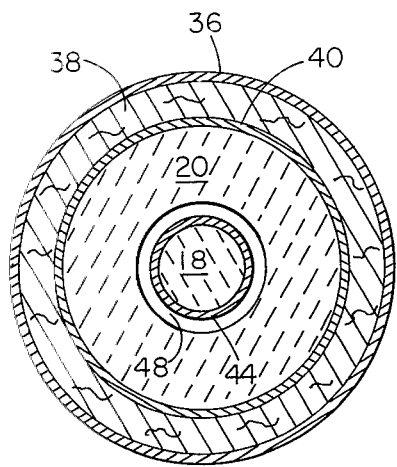
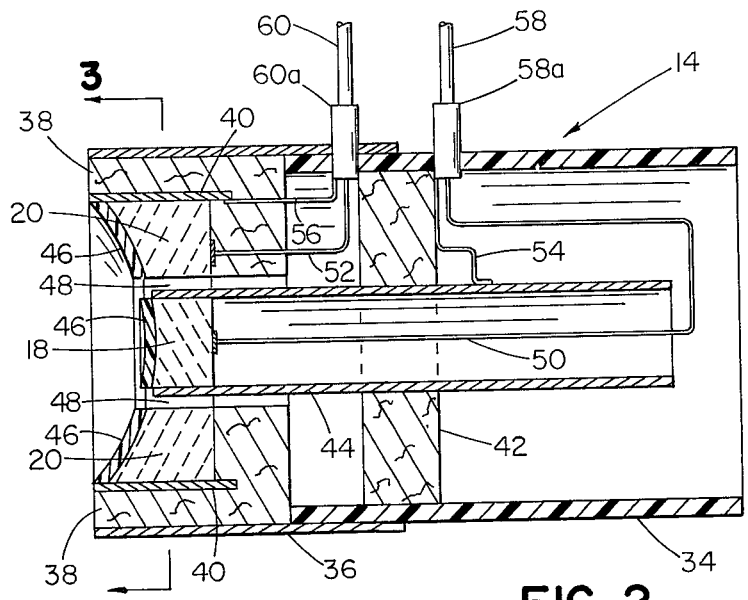
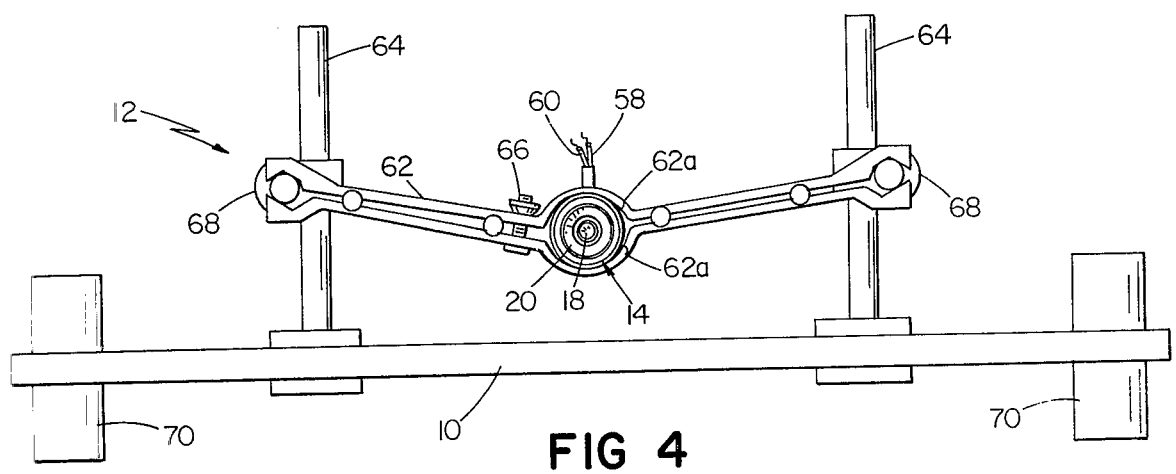

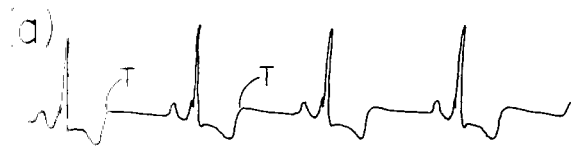
(a)
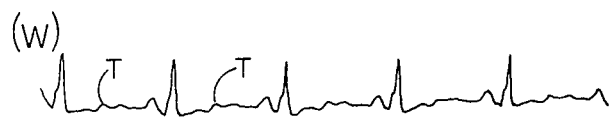
(w)
(b)
(x)
(c)
(y)
(d)
(z)
FIG 5
FIG 6
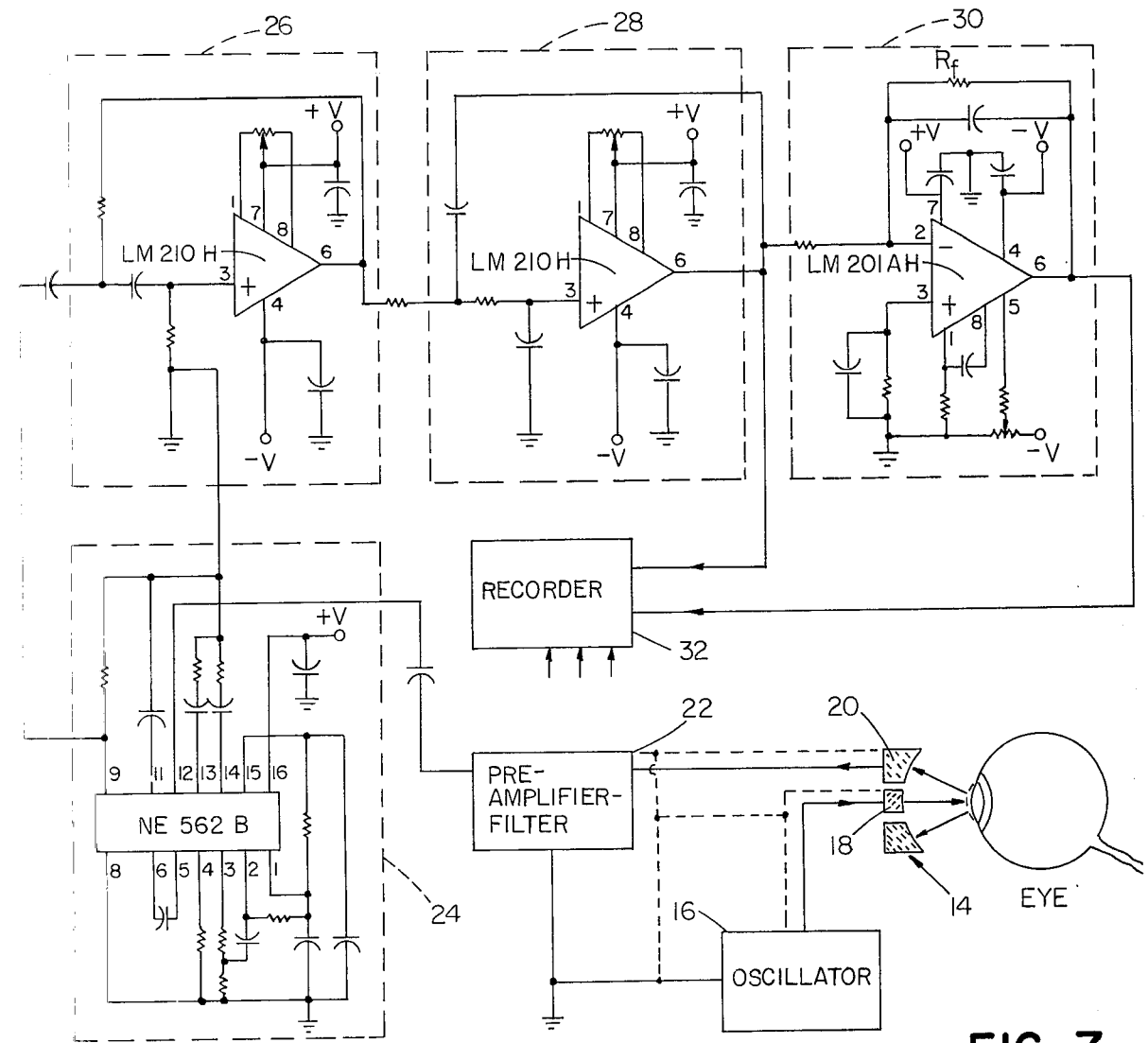
FIG 7

METHOD OF MEASURING OCULAR PULSE

BACKGROUND OF THE INVENTION

This invention relates to the detection and recording of biological pulses and blood flow, and particularly to ophthalmodynamometers.

For the last decade there has been growing interest in the use of ultrasound for medical diagnosis, especially in ophthalmology. A procedure has been developed for transmitting ultrasonic waves into the eye to obtain intraocular images as well as characteristic signals relating to intraocular structure and pathology such as tumors. One device for accomplishing these objects is shown in Carlin U.S. Pat. No. 3,371,660. A second procedure, known as Doppler Sonography, measures circulation in the ophthalmic vascular supply by measuring the Doppler frequency shift in an ultrasonic wave reflected from the circulating blood. Both ultrasonic procedures involve touching either the skin or corneal surface in order to minimize attenuation phenomena associated with ultrasonic propagation through air. Often a liquid medium is interposed between the ultrasonic transducer and the eye to match transducer-tissue impedances so that the maximum ultrasound is transmitted into the eye rather than reflected from its surface, one example being shown in Giglio U.S. Pat. No. 3,453,998.

A second area of interest is in the use of tonometry in diagnosing ophthalmic disorders, especially glaucoma. Tonometry covers a variety of procedures for measuring intraocular pressure and volume changes. A common method, electronic tonometry, involves placing a calibrated piezoelectric weight on the corneal surface to record intraocular pressure and volume changes to detect, for example, the elevated intraocular pressure caused by glaucoma. A local anesthetic is administered to a patient, an ophthalmologist trained in the use of an electronic tonometer is used, and the test takes about 5 minutes. Recently, tonometric procedures have been proposed to avoid touching the eye. In Lichtenstein et al. U.S. Pat. No. 3,545,260 a gas under pressure is utilized to depress the cornea. Ultrasonic pulses are then transmitted to and reflected from the cornea; the pulse-return time delay caused by the increased pulse path due to the corneal depression is then correlated with intraocular pressure to detect glaucoma. Another method, shown in Hobbs U.S. Pat. No. 3,613,666, involves placing an ultrasonic transducer next to the eyelid without touching the eye itself in order to vibrate the eye, transmitting a light beam to the eye, and detecting either a change in the amount of reflected light or a change in the direction of propagation of the reflected light, each caused by the eye vibrations. These changes are likewise correlated with intraocular pressure. In general, these tonometric techniques, as with the ultrasonic methods previously discussed, involve either directly touching the eye or applying to it some external force such as gas pressure or acoustical vibration.

A third area of medical interest is in ophthalmodynamometry, which involves measurement of the ocular pulse, as a diagnostic tool for a variety of ophthalmic and circulatory diseases. The physiology of the ocular pulse, a subject of much study, is explained as follows. The blood supply into the choroid layer of the eye is derived from the ophthalmic artery, which is itself a branch of the internal carotid artery. The internal and external carotid arteries arise from a bifurcation of the common carotid artery, the latter originating on the aortic arch. It is at or near the bifurcation of the common carotid artery that much vascular occlusive phenomena occur. As the heart beats, a pressure wave caused by the pulsating blood flow will arrive at the choroid layer, and generate a pressure pulse at the retina. This pressure pulse is propagated through the intraocular medium to the cornea. The cornea distends slightly (1–50 microns) in response, and reverts back to its resting shape in the diastolic portion of the heartbeat. This phenomenon is known as the ocular pulse. Although this motion of the eye is caused by the ocular pulse, the fine structure of this motion is a function of the elastic properties of corneal tissue, mechanical motions of intraocular medium, and spatial distribution of ocular blood flow.

Studies by Best et al. ("Graphic Analysis of the Ocular Pulse in Carotid Occlusion," Archives of Ophthalmology, March, 1971, vol. 85, pp. 315–319; "Ophthalmodynamometry and Ocular Pulse Studies in Carotid Occlusion," ibid., March, 1971, vol. 85, pp. 334–338; and "Ocular Pulse Studies in Carotid Stenosis," ibid., June, 1971, vol. 85, pp. 730–737) and by Horven and Nornes ("Crest Time Evaluation of Corneal Indentation Pulse," Archives of Ophthalmology, July, 1971, vol. 86, pp. 5–11) have shown that alterations in the ocular blood supply associated with carotid artery occlusions are reflected in distortions in the shape, amplitude, and duration of the ocular pulse. Conversely, it has been noted that relative differences between left and right ocular pulses are correlated with certain pathological states (e.g., glaucoma or abnormal cerebral circulation).

Specifically, it is desirable to obtain an accurate reading of the ocular pulse in its unbiased, natural state to get the maximum benefit from this physiological monitor. A sensitive pulse reading as an indicator of carotid blood flow can be used to detect, in its incipient stages, vascular occlusive matter, which, if allowed to continue, can cause emboli, leading to cerebral hypoxia, the phenomenon known as a "stroke." Ordinarily the detection of vascular occlusive matter has been accomplished by injection of a radio-opaque bolus into the carotid circulation followed by angiography. This procedure is not used until late in the occlusive process when candidates can be detected by symptoms.

Secondly, glaucoma can likewise be correlated to the ocular pulse before the patient becomes symptomatic.

Thirdly, elevated or otherwise abnormal circulation in the major arteries supplying the cerebral hemispheres will be reflected in the ophthalmic arteries and can be seen in changes in the parameters of the ocular pulse.

Finally, a wide range of other pathologies leading to distortions in the ocular pulse can be screened for by a careful, sensitive measurement of the pulse. Although discrimination between pathologies would require further diagnostic procedures as well as observation of clinical signs and symptoms, ocular pulse distortions would alert a physician to the necessity for additional tests. Exemplary of these other pathologies are orbital cellulitis, cavernous sinus thrombosis, retinopathies (arteriosclerotic and hypertensive), papilledema, and pulseless disease.

Measurement of the ocular pulse, as noted, is done by ophthalmodynamometry, which presently utilizes the tonometric techniques already discussed that involve touching the eye. See, e.g., Bron et al., "Tonographic Studies in Carotid Occlusive Disease," British Journal of Ophthalmology, 1967, vol. 51, pp. 577–595. Best et al. in the articles discussed above utilize a suction cup contacting the eye. Another method involves looking into the eye to watch the pulsation of the retinal artery. Visual methods also involve biasing the eye to produce a pulse large enough to be resolved visually. A third method that has been attempted to avoid contacting the eye is an interferometric technique in which motion due to the ocular pulse is ideally correlated with a changing light interference pattern.

SUMMARY OF THE INVENTION

The invention provides a no-touch, safe, easy to use, sensitive and accurate ophthalmodynamometer, and further provides a low-noise, compact and simple ultrasonic transducer assembly.

The invention provides for measuring the ocular pulse ultrasonically not only without touching the eye but also without indirectly applying any biasing force to the eye. The invention obtains a measure of the ocular pulse in its free running, unbiased state, displaying the fine structure of the pulse associated with this natural state. It provides a direct readout of the velocity-time waveform associated with the ocular pulse as well as the displacement-time waveform. The invention can discriminate between motion related to the ocular pulse and unwanted eye motion and other noise. By presenting a sensitive, accurate display of the ocular pulse in its natural state, the invention provides a mass screening device for the wide variety of diseases which cause distortions in the ocular pulse, including carotid occlusion, potential stroke (in its early stages), glaucoma and other eye and circulatory pathologies. Further, by permitting easy simultaneous measurement and comparison of the ocular pulses of both eyes, differences between the pulses correlated with pathologies are readily detected. Finally, the invention can be adapted to measure other biological pulsations besides the ocular pulse.

During testing, the eye need not be kept absolutely still, nor need it be anesthetized, and the procedure is not traumatic. The energy levels used are substantially below the threshold damage level to the cornea. Precise alignment of the eye with the apparatus and maintenance of exact eye-apparatus distances are not necessary. Testing can be done in a matter of seconds by a technician without the need for an ophthalmologist, and the test results can be processed rapidly by compact and inexpensive conventional integrated circuitry. In particular, F.M. demodulation circuitry can be used so that the information carried by the signal is independent of its amplitude and hence attenuation of the signal in the air presents no serious problem. In fact, the invention takes advantage of the air-eye tissue impedance mismatch in that most of the ultrasonic energy transmitted to the eye is reflected back for processing rather than passing into the eye.

The transducer assembly of the present invention is easy to make, and minimizes acoustical, electrical and mechanical cross talk between its transmitter and receiver while conveniently housing them together for optimum reception of reflected return signals. Further, the transmitted energy is substantially collimated over its depth of field, enabling accurate direction of the energy against an object placed within the depth of field.

The invention features in one aspect an ophthalmodynamometer comprising a transmitter for transmitting continuous wave ultrasonic energy to an eye, a receiver for receiving the energy reflected back from the eye, a support assembly for positioning the transmitter and receiver in spaced relation to the eye, and demodulation circuitry connected to the receiver for detecting a modulation in the reflected energy caused by a pulsation of the eye and for providing a signal in response to the modulation. The invention features in another aspect an ultrasonic transducer assembly comprising a transmitter comprising an ultrasonic transducer having a concave face portion for transmitting focused ultrasonic energy to an object, a receiver comprising an ultrasonic transducer for receiving the ultrasonic energy reflected from the object while the transmitter is still transmitting ultrasonic energy, and a housing for maintaining the transmitter and the receiver in spaced relation to provide acoustical isolation between the transducers.

Certain preferred embodiments feature demodulation circuitry comprising a frequency demodulator for detecting the Doppler frequency shift in the reflected energy relative to the transmitted energy caused by the pulsation of the eye and for providing a signal proportional to the shift; a frequency demodulator comprising a phase locked loop; demodulation circuitry further comprising an amplifier for amplifying the modulated, reflected energy, a frequency-selective filter for attenuating energy received by the receiver at other frequencies than the frequency of the modulated, reflected energy, an integrator for providing a second signal proportional to the displacement of the pulsating eye as a function of time, and a recorder for displaying and recording the signals; demodulation circuitry further comprising a second frequency-selective filter for attenuating energy coming from the frequency demodulator at other frequencies than the frequency of the signal provided by the demodulator and wherein the amplifier is an automatic gain-controlled amplifier; a receiver having a concave face portion; a generally annular transducer and a smaller transducer surrounded by the annular transducer; the receiver as the annular transducer and the transmitter as the smaller transducer; a transmitter adapted to transmit continuous wave ultrasonic energy which will be reflected back from the surface of the eye and received by the receiver; a transmitter having a depth of field from 15 to 50 mm.; the transmitter as the annular transducer and the receiver as the smaller transducer; a transmitter adapted to transmit ultrasonic energy having a frequency from 100 KHz to 10 MHz; a transmitter which has an F/No. from 1 to 25; a transmitter adapted to transmit the ultrasonic energy through a gaseous atmosphere to the eye and a receiver adapted to receive the energy reflected from the eye through the gaseous atmosphere; a support assembly comprising an adjustable clamp holding the transmitter and receiver for varying the position of the transmitter and receiver with respect to the eye; and a transmitter comprising a pair of ultrasonic transducers and a receiver comprising a second pair of ultrasonic transducers for concurrently transmitting to and receiving from two eyes the ultrasonic energy to provide a signal for each eye, which signals are then compared. Other preferred embodiments feature demodulation circuitry comprising an amplitude demodulator for detecting the change in amplitude in the reflected energy caused by a pulsation of the eye and for providing a signal which is proportional to the amplitude change.

Other advantages and features of the invention will be apparent from the description and drawings herein of preferred embodiments thereof.

BRIEF DESCRIPTION OF THE DRAWINGS

FIG. 1 is a block diagram of one embodiment of the present invention.

FIG. 2 is a sectional view, along a vertical plane, of a transducer assembly embodiment of the present invention.

FIG. 3 is a sectional view through 3—3 of FIG. 2.

FIG. 4 is a front elevation view of apparatus used in one embodiment of the present invention.

FIG. 5 comprises a series of graphical displays associated with one embodiment of the present invention.

FIG. 6 comprises a further series of graphical displays associated with the embodiment of FIG. 5.

FIG. 7 is an electrical schematic corresponding to one portion of the block diagram of FIG. 1.

DESCRIPTION OF THE PREFERRED EMBODIMENT

Figure 9:
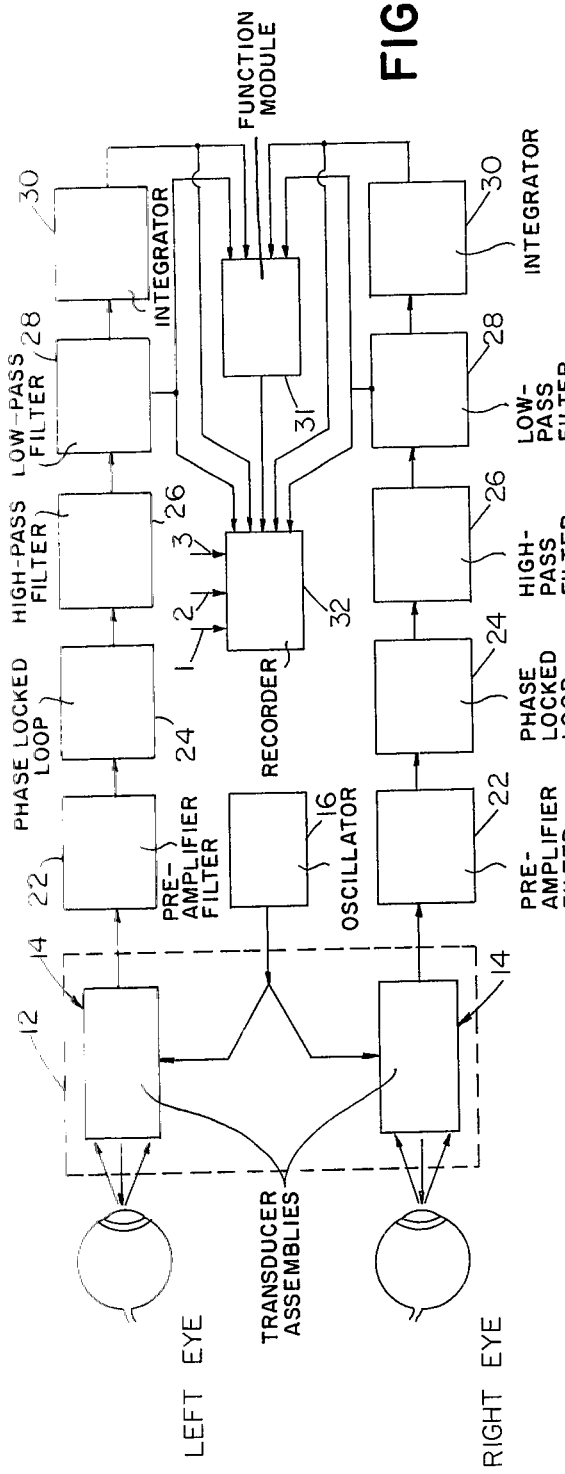
FIG. 9 is a block diagram of another embodiment of the present invention.

There is shown in FIG. 1 an ophthalmodynamometer comprising support assembly 12, transducer assembly 14, oscillator 16, and demodulation circuitry 21.

A subject bites on bite board 10 connected by support assembly 12 to transducer assembly 14. The transducer assembly is positioned so that the subject stares straight ahead into it but also so that the corneal surface does not touch it. While apparatus for use with one eye is described with reference to FIG. 1, additional transducers and circuitry may be provided so that both eyes may be concurrently examined, as will be described with reference to FIG. 9.

Oscillator 16 produces a continuous sinusoidal voltage with frequency $f_c$ equal to 1MHz. The voltage is of the form $\sin(w_c t)$ where $w_c$ equals $2\pi f_c$. This voltage is coupled into focused transmitter 18 of transducer assembly 14, which produces continuous ultrasonic wave energy having a frequency of 1MHz that is propagated to the surface of the eye. The transmitted energy is substantially collimated and about 2 to 3 mm. in diameter, starting from about 21.75 mm. from transmitter 18 and continuing for a depth of field of about 15 mm. The distance from the transducer assembly to the eye is preferably chosen from 21.75 to 36 mm. so that the corneal surface will be somewhere within the depth of field. For transducer assembly 14, optimum return signals are obtained in this distance range. The energy is reflected from the moving corneal surface, and received by focused receiver 20 of assembly 14.

Because the corneal surface moves toward, then away from, assembly 14 due to its distention and contraction by the ocular pulse, continuous wave ultrasonic energy hitting this moving surface will be reflected back at a different frequency because of the Doppler effect. Specifically, the shift or change in reflected carrier frequency ($\Delta f_c$) of an incident wave front striking a moving surface is given by:

$$\Delta f_c = 2\frac{v(t)}{c}\cos\theta \quad (1)$$

where
- $\Delta f_c$ = change in interrogation frequency $f_c$,
- $v(t)$ = velocity of the object being interrogated, a function of time $t$,
- $c$ = velocity of the wave front in media, and
- $\theta$ = angle of incidence of the wave front.

The reflected beam is thus frequency modulated, because the frequency shift, $\Delta f_c$, carries information about corneal surface velocity.

Receiver 20 converts the ultrasonic return energy back to an electrical signal of the form $A \sin[(w_c + \Delta w_c)t]$, where $\Delta w_c$, the angular frequency shift, equals $2\pi \Delta f_c$ and A is the varying peak amplitude of the return signal. This signal is then coupled into demodulation circuitry 21, which comprises preamplifier-filter 22, phase locked loop 24, high-pass filter 26, low-pass filter 28, integrator 30 and recorder 32. The signal is first coupled into preamplifier-filter 22, which has a band-pass filter stage and an automatic gain-controlled amplifier stage. The band-pass filter stage has low and high frequency breakpoints bracketing the modulated frequency ($w_c + \Delta w_c$) in order to eliminate noise. The amplifier stage multiplies the input signal by a varying gain ($\Delta G$) which is inversely proportional to the varying amplitude A to provide a signal having a substantially constant peak amplitude.

The output of preamplifier-filter 22, represented by $\Delta GA \sin[(w_c + \Delta w_c)t]$, is then coupled into phase locked loop 24. The phase locked loop demodulates the frequency modulated signal by extracting from the signal an output which is proportional to the frequency shift, $\Delta w_c$. The loop accomplishes this through the following feedback procedure. The loop initially generates its own reference signal, $w_l$, which it compares with an incoming signal to determine both the frequency and phase difference between the signals. When there is a frequency difference, the loop will generate an error voltage $\Delta V_o$ that is proportional to the frequency difference. $\Delta V_o$ is part of the D.C. output of the loop, $V_o$. $V_o$ is fed back to vary the loop reference frequency $w_l$ until it equals the incoming signal frequency and to change the phase of the reference signal until it is exactly 90° out of phase with the incoming signal. The loop reference signal is then "locked" into this phase relationship with the incoming signal, and thus it will follow any subsequent change of phase in the incoming signal. The whole feedback procedure is repeated for subsequent frequency changes in the incoming signal. It follows that when the loop reference frequency $w_1$ and the frequency $w_c$ of the wave transmitted to the eye are initially equal, which is accomplished by adjusting the frequency of oscillator 16 so that $w_c$ equals $w_l$, the loop output will be proportional to the Doppler shift, $\Delta w_c$. That is, $$\Delta V_o = \Delta w_c / K_o \quad (2)$$

where
- $\Delta V_o$ = the change in the phase locked loop demodulated output voltage,
- $\Delta w_c$ = the change in the input carrier frequency, and
- $K_o$ = the conversion (D.C. to A.C.) gain of the phase locked loop.

Combining equations (1) and (2) the changing D.C. voltage is given by, $$\Delta V_o = \frac{4\pi v(t)\cos\theta}{cK_o} \quad (3)$$

$\theta$, the angle of incidence, varies so little from 0° when the eye is staring at the transducer that it may be considered a constant. Thus the demodulated output of the phase locked loop is proportional to the velocity of the surface being interrogated. That is, $$\Delta V_o = Kv(t) \quad (4)$$

where $K = 4\pi\cos\theta/cK_o$ is a contant. The signal $\Delta V_o$ is thus a direct representation of the velocity of the corneal surface as a function of time.

The signal coming from the phase locked loop may contain unwanted artifacts arising in the following two ways: first, slow, varying motion in either or both the ambient air and the corneal surface (not caused by the ocular pulse) shows up as a very low frequency signal (normally about 0.5 Hz) on which the ocular pulse signal (about 5 to 10Hz) is superimposed; and second, the high frequency (here 1MHz), low amplitude loop reference signal $w_l$ used to do frequency and phase comparison in the loop is superimposed on the ocular pulse output signal. High-pass filter 26 removes this slow varying, low frequency component coming from loop 24, and low-pass filter 28 removes this high frequency carrier component. Thus the combined effect of filters 26 and 28, which are actually amplifiers with unity gain above and below respective low and high frequency breakpoints, is to provide a band-pass filter allowing only the ocular pulse, corneal velocity signal to get through. To obtain a sharply defined band-pass around the ocular pulse signal so as to eliminate the maximum amount of noise, filters 26 and 28 are chosen to produce a Butterworth-Thomson response curve.

The output of filter 28 is coupled into recorder 32 to give a readout of the velocity of the corneal surface as a function of time. The output of filter 28 is also coupled into integrator 30, which integrates the velocity-time output to provide a displacement-time signal, which is then coupled into recorder 32 to give a readout of the position (displacement) of the corneal surface as a function of time. Integrator 30 acts as a simple constant gain amplifier for frequencies lower than the ocular pulse to provide D.C. stability. The additional arrows into recorder 32 indicate reference wave inputs such as the electrocardiogram.

There is shown in FIGS. 2 and 3 a more detailed view of assembly 14. The transducer housing comprises a hollow plastic tube 34 press-fitted within metal sleeve 36 having a thickness of 0.2 mm. and an inner diameter of 20 mm., the housing having a total length of 35 mm. Tightly fitted into the end of sleeve 36 is cork ring 38 having a hole diameter of 6.0 mm. and an axial length of 10 mm. An annular section 15.6 mm. in diameter and 6 mm. inward from the end of sleeve 36 has been removed from ring 38 to receive a metal tube 40 of 0.2 mm. thickness and 7 mm. long. About a 1 mm. deep circular groove has been cut into ring 38 to seat tube 40. Press fitted within ring 38 is focused transducer receiver 20, a piezoelectric ring made of barium titanate ($BaTiO_3$) and having in its outer face a spherical concave shape with a radius of curvature of 21.75 mm. The hole diameter of the receiver is 6.0 mm. Spaced from cork ring 38 by about 5 mm. is cork ring 42 having a hole diameter of 5.4 mm. and being about 5 mm. thick. Fitted within ring 42 is metal tube 44, about 24 mm. long and extending through the hole in cork ring 38. Fitted into the end of tube 44 so that its back face is aligned with that of receiver 20 is focused transducer transmitter 18, a piezoelectric cylinder of barium titanate. The front face is spherical and concave with the same radius of curvature as has receiver 20. An epoxy resin layer 46 of a thickness of 0.2 mm. coats the concave faces of transmitter 18 and receiver 20. Because its index of refraction is intermediate to that of air and barium titanate, it serves to lower the air-crystal impedance mismatch so that ultrasound may be coupled between the transducer and air with minimum losses due to reflection at the interface. The coating may be any thickness which is an integral multiple of 1/4 of the ultrasonic wavelength, and will thus act as an interference filter. Isolating metal ring 44 and transmitter 18 from receiver 20 is annular air gap 48, 0.3 mm. wide.

Deposited on the back face of transmitter 18 and receiver 20 is a thin conductive metal coating, to which are respectively soldered transmitter lead 50 and receiver lead 52. Transmitter ground lead 54 and receiver ground lead 56, which are isolated from each other by ring 42 and by plastic tube 34, are respectively connected to tube 44 and tube 40. Coaxial cables 58, 60 with their metal connectors 58a, 60a fitted respectively through apertures in tube 34 and sleeve 36, respectively couple the transmitter leads to oscillator 16 and the receiver leads to preamplifier-filter 22.

In operation, a sinusoidal signal from oscillator 16 enters transmitter 18 through lead 50, causing the resonant crystal to vibrate and thereby emit continuous wave ultrasonic energy having a frequency of 1MHz. Cork rings 38 and 42 and air gap 48 provide primarily acoustical but also electrical and mechanical isolation between transmitter 18 and receiver 20 so that noise due to cross talk of all types is kept down to an acceptable amount of about 1 microvolt. The emitted waves, as previously noted, are collimated over a depth of field into a 2 to 3 mm. diameter beam. If the eye is placed within the depth of field, the beam strikes the cornea over a small and very gently curved area so that the phase delays and resultant interference between reflected waves are small and hardly affect the return signal. Also, the angle of incidence varies at most by minutes of arc from 0° so that substantially all of what is reflected back out of this on-axis signal will be collected by focused receiver 20. The corneal tissue—air interface creates a substantial impedance mismatch for ultrasound so that very little energy is transmitted intraocularly, most being reflected from the corneal surface. Although the power level used is safely at least two orders of magnitude less than 2.5 watts/cm², the damage threshold to the cornea, there is sufficient return signal to be easily detected. Likewise, the attenuation of the ultrasonic signal in the air, which is severe at these high frequencies even over the small distances here involved, has little effect on the quality of the return signal, which, because it is frequency-modulated, carries information that is independent of the amplitude.

The position of transducer assembly 14 is adjustable in support assembly 12 (FIG. 4), comprising clamp 62, support poles 64, bite board 10, and posts 70. Clamp 62 has a pair of curved clamping members 62a which by means of screw 66 grip the transducer housing. Clamp 62 is freely moveable, and, in cooperation with adjustable clamp supports 68, allows transducer assembly 14 to be raised, lowered, moved laterally and toward or away from the eye. Support poles 64 are connected to wooden bite board 10, which in turn is supported by posts 70. By having the subject bite bite board 10, the head is held stationary while the transducer is positioned. The optimum distance between eye and transducer is obtained by displaying the signal reflected from the eye on an oscilloscope before the signal is processed by elements 22 to 30. With the subject staring straight ahead, it requires a few seconds to adjust the position of transducer assembly 14 until the return signal is maximized.

The return signal is then processed by the apparatus of FIG. 1 with a standard Grass polygraph serving as recorder 32. A typical velocity-time readout is shown in FIG. 5, and a typical distance-time readout shown in FIG. 6. In FIG. 5, (a) shows a human subject's electrocardiogram (ECG), taken in the Einthoven triangle configuration with the upper leads on the lateral chest wall, (b) is a one-second time marker, (c) is the corneal surface velocity-time plot, and (d) is a myographic trace of extraocular muscle activity. The almost sinusoidal pulsations in (c) represent the velocity of the corneal surface as it is distended and then undergoes a damped oscillation back to equilibrum. The profile shown is that of free-running corneal motion, since no weight or other pressure biases the natural eye movement responsive to the ocular pulse. It is well known that the systolic peak in the aorta occurs near the beginning of the T-wave, designated T in (a). It can be seen that the ocular pulsations in (c) are contiguous with this region of the ECG, as would be expected. The low level myographic trace (d) due to the signal picked up by electrodes connected around the orbit of the eye shows that the signal in (c) is not caused by involuntary muscular eye movement, which produces a phase shift on the order of 1/1000 of the ultrasonic wavelength when staring, whereas the ocular pulse is on the order of ¼ wavelength and produces a signal about 250 times stronger. Even when the eye is tracking the motion of a sine wave on an oscilloscope, the noise caused by this motion is still well below the ocular pulse signal level, since the phase shift caused by tracking is about 1/500 of a wavelength. In FIG. 6, (w) is a human subject's ECG, (x) is the one-second time marker, (y) is the corneal surface displacement (from the transducer)-time plot, and (z) is a graph of the carotid pulse made by a conventional pressure transducer touching the neck. The biphasic appearance of each pulse in (y), with the dicrotic notch between each pair of peaks, is characteristic of the ocular pulse. As with the velocity profile, the displacement profile is correlated to the ECG and its T-wave, designated T in (w), but it is also correlated to the carotid pulse displayed in (z).

FIG. 7 shows a circuit corresponding to the block diagram of FIG. 1. Oscillator 16 is a General Radio Model 1310-A Oscillator. Preamplifier-filter 22 is described in more detail in FIG. 8. Phase locked loop 24 is a Signetics NE 562 B Phase Locked Loop (integrated circuit) with its terminals connected as shown. High-pass filter 26 and low-pass filter 28 each employ National Semiconductor Operational Amplifier LM 210 H with the terminals connected as shown to perform the high-pass function in 26 and the low-pass function in 28. Integrator 30 employs National Semiconductor Operational Amplifier LM 201 AH with the terminals connected as shown to perform the integration function. Resistor $R_f$ provides negative feedback and thus D.C. amplifier amplifier stability for signals of lower frequency than the ocular pulse.

Figure 8:
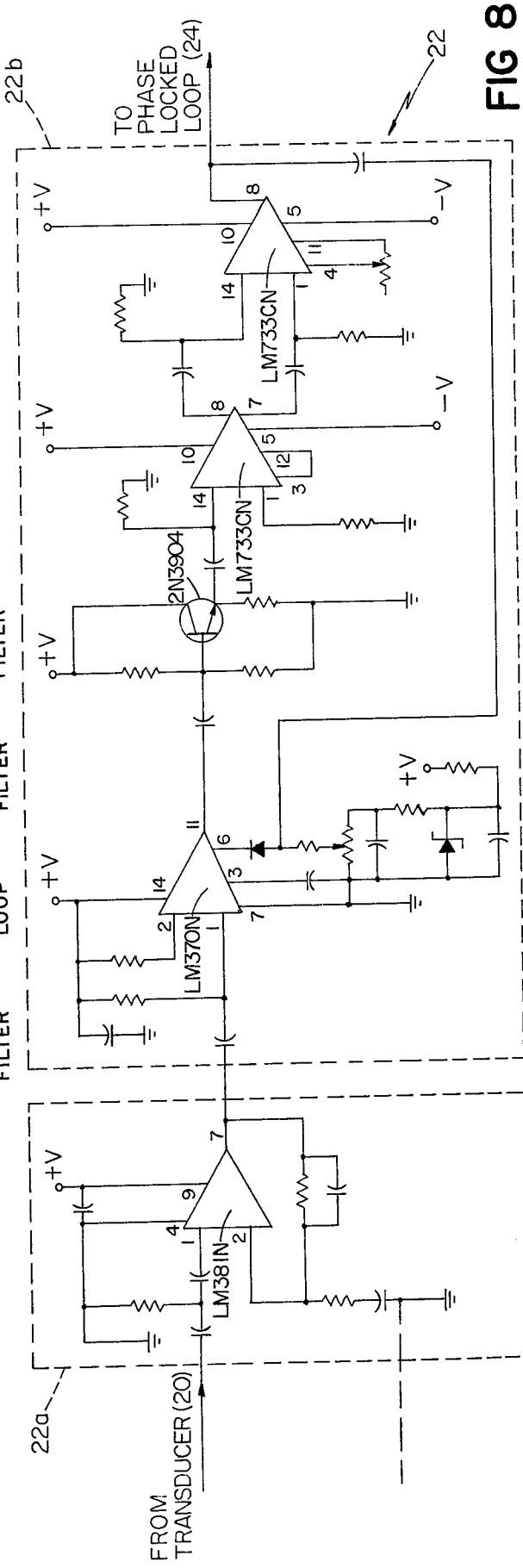
FIG. 8 is an electrical schematic corresponding to another portion of the block diagram of FIG. 1.

Circuitry for preamplifier-filter 22 as shown in FIG. 8 comprises two stages, a band-pass filter 22a and an automatic gain-controlled amplifier 22b. Band-pass filter 22a uses National Semiconductor Operational Amplifier LM381N with the terminals connected as shown, and amplifier 22b uses National Semiconductor Operational Amplifiers LM370N and LM733CN and a 2N3904 transistor all connected as shown. Though not preferred, a Tektronix Model 561B Oscilloscope with Preamplifier Model 3A9 could be used as preamplifier-filter 22.

The arrangement of the apparatus for simultaneous measurement of the ocular pulses of both eyes is shown in FIG. 9. A pair of matched transducer transmitters and receivers powered by a common oscillator 16 and mounted on support assembly 12, adapted to hold two transducer assemblies, with two sets of receiver circuitry identical to that described for one eye is utilized, with the addition of function module 31 connected between low-pass filters 28 and recorder 32 and also between integrators 30 and recorder 32. Function module 31 is a subtracter whose output is the difference between the right and left waves, although a variety of analog or digital devices could be used here depending on how one wished to process the two waves. As shown, the right and left outputs also bypass the function module to be fed directly into recorder 32. Also shown are inputs 1, 2, and 3 to be the recorder, for the ECG, the carotid pulse, and other desired reference waveforms.

Regarding modifications in application and structure, the ultrasonic signal can also be beamed against the sclera of the eye, although because of the nature of this tissue more damping occurs so that the return signal is not as strong as that reflected from the cornea. As to distance between the eye and transducer, the farther the signal must travel, the more energy must be put into the signal so that the danger of transmitting too much energy into the eye increases at long distances. Preferably the depth of field should range from 15 to 50 mm., the specific value being determined by the F/No. of the transmitter and the ultrasonic frequency selected. For a frequency range of 100KHz to 10MHz, the F/No. can range from 1 to 25.

As to the transducers, any commercially available ultrasonic materials, especially piezoelectric materials, which can be made to exhibit resonances in the preferred frequency range are suitable. The following are included: pure piezoelectric materials such as quartz or rochelle salt; piezoelectric ceramics of perovskite, distorted perovskite, or non-perovskite structure (e.g. Ba Ti $O_3$, Pb (Ti, Zr) $O_3$, Na $N_b$ $O_3$, and Na $N_b$ $O_3$ with K, Pb, or Cd substituted for Na); magnetic ceramics which can generate ultrasound at the desired frequencies; and other materials which can be used to generate ultrasound such as the ferromagnetic elements, ferrites, and ferroelectric alloys. As to the air-transducer impedance matching coating, any material or materials, used singly or in discrete layers (the latter having progressively increasing indices of refraction going from the air to the transducer surface), are suitable. Other conventional acoustical damping materials besides cork can be used such as aerated polymer plastics. Other configurations besides the two-piece spherical transducer can be used. The receiver can be a segmented array for multichannel reception. The curvature of the transducer parts can be elliptical, parabolic, or any shape that would maintain acoustical beam integrity across some distance, and indeed the transducer can be flat or otherwise unfocused, although in that case accurate alignment of eye and transducer becomes a more serious consideration. In the transducer assembly described the transmitter could be used as the receiver and the receiver as the transmitter.

As to the method of modulation, frequency modulation (F.M.) offers the best results, but amplitude modulation (A.M.) can also be used. A change in the cornea-transducer distance caused by the ocular pulse will vary the amplitude of the return signal, the weakest (lowest amplitude) signals travelling the farthest and being most attenuated in the air. Furthermore, the total amount of reflected signal (backscatter) will decrease with increasing distance to the reflecting surface. Therefore a continuous measurement of the amount of energy in the return signal can be correlated to changing cornea-transducer distance. Circuitry similar to that described but arranged to perform amplitude demodulation can be used. Because cornea-transducer distance is critical to A.M., unwanted eye motion presents a serious problem to effective use of this method, and must be carefully controlled.

The testing time is a function of the pathology to be diagnosed. Some, such as glaucoma or carotid stenosis, will require application of the signal for only about 10 seconds. Others may require somewhat longer time, but in most cases this time will not exceed 30 seconds. If necessary, repeated or continuous runs can be taken for as long as desired.

Other support assemblies for positioning the transducer in spaced relation to the eye besides support assembly 12 can be used such as a headpiece with a built-in pair of transducers.

The invention need not be restricted to measuring the ocular pulse. Biological movements throughout the body can be measured such as the radial pulse and vascular blood flow. Such readings may, however, not be as free from noise as the ocular pulse, one reason being intervening tissue between the transducer and the source of motion. The invention can alternatively be used in the conventional touch mode by placing the transducer on the neck or wrist, for example, to measure the carotid or radial pulse.

Other embodiments within the invention will be apparent to those skilled in the art.

What is claimed is:

1. A method of observing pulsations in an eye comprising the steps of:
    positioning said eye to receive continuous wave ultrasonic energy,
    transmitting continuous wave ultrasonic energy to said eye from a source spaced from said eye,
    receiving said energy reflected back from said eye, and
    detecting a modulation in said reflected energy caused by a pulsation of said eye and providing a signal in response to said modulation.

2. The method of claim 1 wherein said transmitting step further comprises transmitting said continuous wave ultrasonic energy through a gaseous atmosphere to said eye from said source and said receiving step further comprises receiving said energy reflected back from said eye through said gaseous atmosphere.

3. The method of claim 1 wherein said detecting step comprises frequency demodulating the Doppler frequency shift in said reflected energy relative to said transmitted energy caused by said pulsation and providing a signal which is proportional to said frequency shift.

4. The method of claim 3 further comprising the step of focusing said transmitted continuous wave ultrasonic energy.

5. The method of claim 1 wherein said transmitting step comprises transmitting said energy to the surface of said eye and wherein said energy is reflected back from said surface.

6. The method of claim 1 wherein said transmitting step comprises transmitting continuous wave ultrasonic energy to two eyes concurrently and said detecting step further comprises comparing said modulations from each said eye.

* * * * *

Dedication 3,948,248.—*Joel L. Zuckerman,* West Hartford, and *Harry J. Grossman,* West Willington, Conn. METHOD OF MEASURING OCULAR PULSE. Patent dated Apr. 6, 1976. Dedication filed Aug. 12, 1981, by the assignee, *University of Connecticut.*

Hereby dedicates to the Public the remaining term of said patent.
[*Official Gazette March 8, 1983.*]